United States Patent [19]

Kazen et al.

[11] 4,253,830

[45] Mar. 3, 1981

[54] AUTOCLAVABLE DENTAL BUR BLOCK

[75] Inventors: Douglas H. Kazen, Kirkland; Rudy F. Dengah, Seattle, both of Wash.

[73] Assignee: North Pacific Dental, Inc., Kirkland, Wash.

[21] Appl. No.: 46,714

[22] Filed: Jun. 8, 1979

[51] Int. Cl.³ ............................................. A61G 1/14
[52] U.S. Cl. ....................................... 433/77; 206/368; 206/379; 211/69
[58] Field of Search ............................ 433/77; 211/69; 206/563, 562, 564, 63.5, 368, 369, 379; 312/209; 46/25

[56] References Cited

U.S. PATENT DOCUMENTS

| | | | |
|---|---|---|---|
| 720,132 | 2/1903 | Green | 211/69 |
| 1,341,848 | 6/1920 | Haensler | 211/69 |
| 2,126,766 | 8/1938 | Gerbermann | 211/69 |
| 2,568,089 | 9/1951 | Pendleton | 206/379 |
| 3,102,637 | 9/1963 | Scholl, Sr. | 211/69 |
| 3,154,192 | 10/1964 | Cowley | 206/379 |
| 3,236,366 | 2/1966 | Broda et al. | 211/69 |
| 3,643,812 | 2/1972 | Mander et al. | 206/563 |
| 3,934,605 | 1/1976 | Legris | 46/25 |
| 3,938,253 | 2/1976 | Barnard et al. | 433/77 |
| 4,050,894 | 9/1977 | Genis | 206/369 |

FOREIGN PATENT DOCUMENTS 1038714 9/1958 Fed. Rep. of Germany ............ 433/77

*Primary Examiner*—Gene Mancene
*Assistant Examiner*—John J. Wilson
*Attorney, Agent, or Firm*—Christensen, O'Connor, Johnson & Kindness

[57] ABSTRACT

An autoclavable dental bur block or portable holder for dental burs and the like having elastomeric insert receptacles adapted to releasably hold burs of different shank diameters, with the receptacles color coded and arrangeable and rearrangeable in organized manner as a convenient means to identify and organize the different kinds of burs in the holder. The tubular insert receptacles have a downwardly tapered central bore, including an upper portion of relatively large average diameter extending above the support panel to accommodate large-shank burs, and a lower portion extending below the support panel to accommodate small-shank burs. Dovetail fitting elements on the sides of the bur blocks adapt them to interengage complemental fittings on other blocks so as to hold a plurality of the bur blocks in substantially coplanar relationship permitting them to be handled as a composite unit.

6 Claims, 6 Drawing Figures

U.S. Patent   Mar. 3, 1981   4,253,830
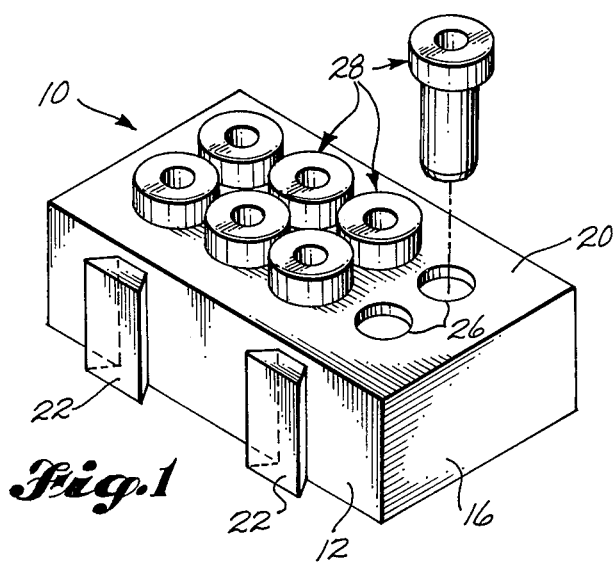
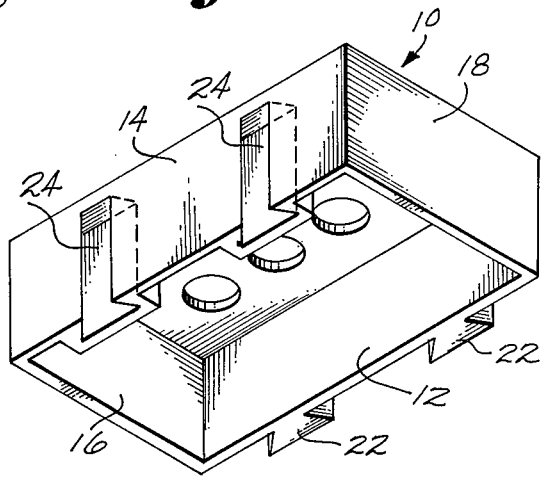
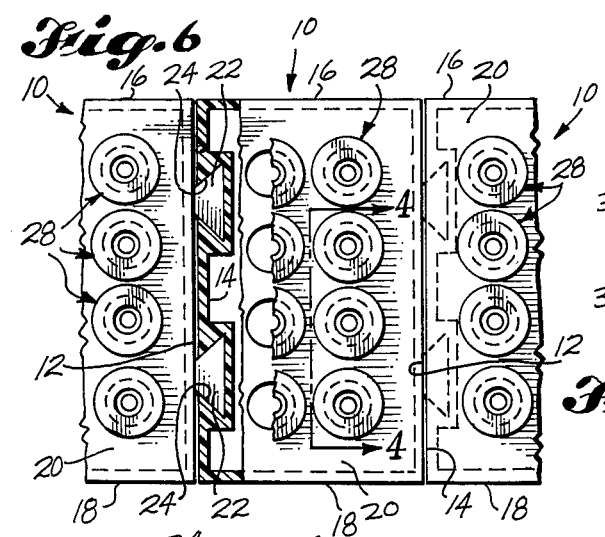
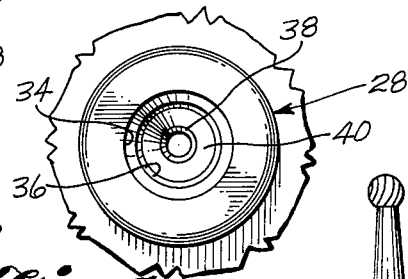
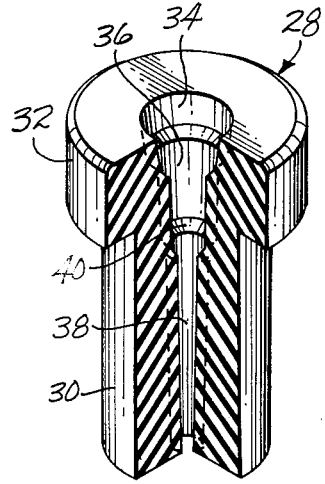
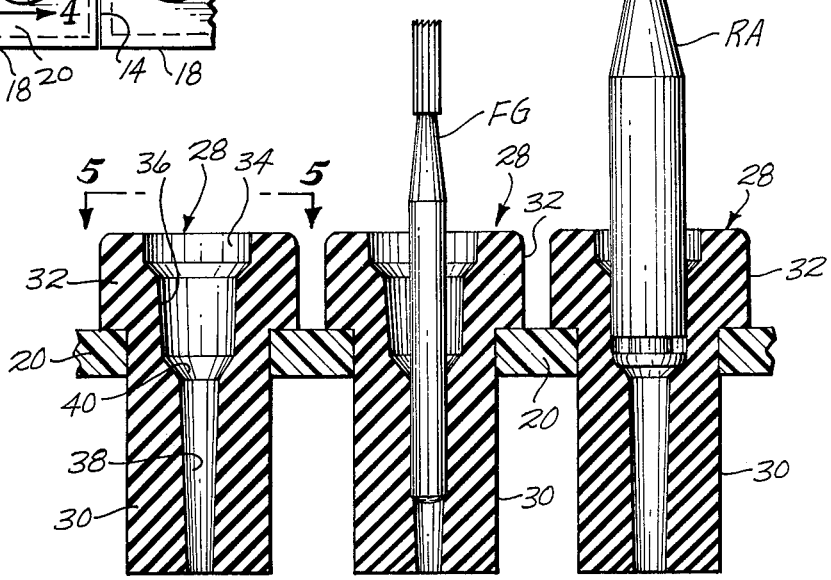

AUTOCLAVABLE DENTAL BUR BLOCK

BACKGROUND OF THE INVENTION

The present invention relates to portable bur blocks for holding dental burs and the like by means of removable elastomeric insert receptacles that may be color coded and arrangeable and rearrangeable in the block in organized manner for ready identification and accessibility, and furthermore to such bur blocks which can be placed in an autoclave for heat sterilization of the burs.

Dental burs (i.e., rotary drills, grinders, etc.) are usually placed in bur blocks on a dental counter or tray preparatory for use or for sterilization. The bur blocks currently available are typically solid wood or solid plastic blocks with a series of socket holes therein to hold the burs by their shanks. Usually the holes in the block are closed at the bottoms so that water entrapped therein can ultimately corrode the bur shanks. If such a bur block is accidentally tipped over the burs ordinarily can drop out. Magnetized stands have also been used to hold the burs along with other tools, but these are somewhat cumbersome to use and are subject to the burs becoming accidentally dislodged. Furthermore, since the shanks of dental burs are of significantly different sizes (FG-Friction Grip) and (RA-Right Angle) when bur blocks are used it has been necessary to provide bur blocks with holes of both sizes.

A broad object of the present invention is to provide an improved bur block overcoming the above-mentioned and related limitations, and more particularly an improved bar block having a group of insert receptacles therein each adapted to hold burs of the different sizes encountered. A related object is to provide such a bur block in which the holding action of the receptacles regardless of bur size is secure yet permits easy bur removal. Still another object is to provide such an improved bur block with removable, rearrangeable insert receptacles that may be differently colored for purposes of identification coding and thereby of organizing the burs in a convenient manner for ready identification and appropriate sequential accessiblity, a significant convenience to the dental operator under busy operating conditions.

A related object of the invention is to provide such a bur block that can be heat autoclaved for sterilization of the burs without damage to the block parts and without water condensate collecting in the bur receptacle sockets.

A further object hereof is to provide an improved bur block having a fitting thereon adapted to engage a complemental fitting on one or more other blocks so as to hold a group of such blocks in coplanar alignment for handling and storage as a composite unit.

BRIEF DESCRIPTION OF THE INVENTION

In accordance with this invention, the improved autoclavable bur block has a base portion adapted to rest on a support surface such as a dental counter or tray and to maintain a holder panel in substantially horizontal position elevated above the support surface. The holder support panel has plurality of mutually spaced receptacle holes therein arranged according to a suitable organizing pattern, and which receive removably a plurality of substantially tubular insert receptacles of autoclavable elastomeric material. Each insert receptacle comprises a tubular body portion open at the top and bottom and extending through the holder panel, with a head portion on the upper end of each receptacle adapted to seat against the top face of the holder panel for locating purposes. Immediately below the flared entrance in its top, the tubular insert receptacle bore starts its downward taper toward the support panel. The upper portion of the bore is of an average diameter to retentively but releasably hold the shanks of the larger (RA) size burs therein; the lower portion of the bore beneath the panel, the shanks of the smaller (FG) size burs. In the preferred embodiment, at about the level of the support panel the receptacle bore steps downward in diameter abruptly. The open bottom of the receptacle bore permits drainage of water condensate. Elastomeric properties of the socket bore walls above and below the support panel permits the burs to be very easily inserted and removed yet to be held securely by the light frictional grip of the wall material on the bur shanks. Different colors assigned to the insert receptacles arranged and rearranged according to selected organizing patterns provides ease of identification and sequential accessibility under operating conditions. Complemental fitting elements on the sides of the holders may be interengaged to lock a plurality of holders in coplanar relationship to permit handling a group of them as a composite unit.

These and other features, objects and advantages of the invention will become more fully evident from the following description by reference to the accompanying drawings.

BRIEF DESCRIPTION OF THE DRAWINGS

FIG. 1 is a top isometric view of the improved bur block according to the present invention with provision for eight elastomeric insert receptacles, six shown installed and one in position for installation;

FIG. 2 is a bottom isometric view of the bur block;

FIG. 3 is an isometric view of an elastomeric tubular insert receptacle, with a portion cut away;

FIG. 4 is a fragmentary elevation section taken on line 4—4 in FIG. 6 and showing one insert receptacle carrying an RA size bur and one an FG size bur;

FIG. 5 is a top face view of one insert receptacle installed; and

FIG. 6 is a top view showing one bur block and adjoining portions of two others with complemental dovetail fitting elements interengaged to permit holding the three bur blocks as a composite unit.

DETAILED DESCRIPTION WITH REFERENCE TO DRAWINGS

In the illustrated preferred embodiment of the invention each bur block 10 is of a box-like configuration including a base portion formed by opposite side walls 12 and 14 and connecting end walls 16 and 18, together with an overlying support panel 20 molded together of hard plastic as a unit. Dovetail fitting tongues 22 in side wall 12 and complemental dovetail fitting grooves or sockets 24 in opposite side wall 14 permit interconnecting a group of the holders in coplanar relationship to be handled as a composite unit. A plurality of holes 26 arranged in suitable patterns, such as in parallel rows, are formed in the support panel 20 to removably receive the elasomeric insert receptacles 28 as shown.

Each of the elastomeric insert receptacles 28 comprises an elongated tubular body 30 having a flange or head portion of 32 at one end adapted to seat in one of the holder panel holes 26 with the flange or head portion contacting the top face of the panel for locating purposes. At its upper end the insert receptacle has a flared or enlarged entrance throat 34 leading downwardly into a socket bore 36 of slight downward taper commencing at a location well above the top face of the support panel 30. Socket bore 36 merges or steps downwardly in diameter into a lower socket bore portion 38 that tapers downwardly to the lower end of the body portion 30 that is open to permit drainage of condensate water. Bore portion 38 also has a slight downward taper.

The relative diameters of the socket bore portions 36 and 38 are such as to receive and retain, through frictional gripping action, the shank portions of dental burs of the two different sizes commonly employed. As shown, the upper sock bore portion 36 is of an average diameter to retentively grip the shank of the RA or right-angle type larger dental bur (FIG. 4) inserted downwardly therein, whereas lower socket bore portion 38 is of a smaller average diameter to retentively grip the shank of the smaller type bore FG type dental bur (FIG. 4). The elastomeric material of the insert receptacles 28 is sufficiently soft and flexible so that insertion and removal of the dental burs is accomplished with very light forces applied downwardly and upwardly when required. The wedging effect on the inserted bur shanks of the slight downward taper of the individual bore, the bore wall elastic properties and the coefficient of friction of the elastomeric wall material provides the desired frictional holding action.

As an additional advantage or feature of the preferred embodiment relating to the ease of insertion and removal of the dental burs without compromising the security of retention of the burs in the elastomeric receptacles if even the holder is tipped over, for example, it will be noted that the major tapered length portion of the upper socket bore portion 36 lies wholly above the constricting aperature wall in the support panel 20. Similarly the major tapered length portion of the lower socket bore portion 38, that is the part of its length that must expand in response to insertion of the shank portion of an FG size dental bur into the same, lies below the lower face of the support panel 20. Accordingly, the expandible walls of the elastomeric receptacle 20 that yield or expand in response to wedging insertion of the socket bore shanks are allowed to expand easily with minimal outwardly directed force against the inside surface of those walls. Ease of insertion and removal conveniently and quickly under operating conditions is thus assured, an important characteristic when a busy dentist or dental technician must move quickly in selecting and removing dental burs for use. It is desirable to be able to remove the burs easily from the holder block without having to hold the block down with one hand while lifting up the bur with the other. At the same time the desired retentive holding action described above is also achieved.

It will also be appreciated that dental burs are of different forms and types particularly with regard to the shape and tooth form of the cutting heads therein. These are typically small elements difficult to see and particularly inconvenient to select if not properly organized for ease of identification. As a further feature of the invention, therefore, the elastomeric inserts 28 may be of different colors each to identify a particular one or more types of burs and these may be easily removed and rearranged in the bur block according to the dentist's operating sequence or preference so that not only are they presented in the desired sequence during an operating procedure to the dentist or the dental technician, but they are readily identified without the necessity of taking time to closely inspect the burs in the block in order to select the correct one for each step in the operating procedure.

It is noted in the preferred embodiment that the upper socket bore portion 36 runs downwardly into the socket bore portion 38 through a definite downward step in diameter 40 occurring approximately in the plane of the support panel 20. If desired, a continuously tapered socket bore may be employed in lieu of a two-part step-connected socket bore. In this case also the taper commences well above the plane of the support panel 20 and continues downwardly well below the plane of the support panel for the reasons and purposes indicated above. It is also noted that the flared entrance throat 30 is a convenience in the preferred embodiment, but that if desired, the entrance of the interior of the tubular insert may be formed simply by the upper end of the tapered upper bore 38 extending fully to the top of the upper end or head portion of the receptacle.

Elastomeric material of suitable softness and flexibility is readily available for the insert receptacles 28 that will withstand the temperature of autoclaves or other heat sterilizing apparatus. For example the insert receptacles may be injection molded of a butadiene rubber such as Shell Oil Company's Kraton G 2705. Such material is thermo-plastic but well capable of standing up under autoclave sterilizing temperatures. Various other materials are also suitable for the purpose. Therefore, the entire unit, including the dental burs rearranged and held in the receptacles of the unit may be inserted into the autoclave, sterilized, and then paced upon the dentist's counter or tray ready for use. Furthermore, if more convenient, a group of such holders may be interconnected using the fitting elements described in order to handle a number of them as a composite unit.

The embodiments of the invention in which exclusive patent rights are claimed are defined as follows:

1. A portable holder for dental burs and the like of the type including an elongated substantially straight cylindrical shank and a rotary cutter formation on one end of the shank, said holder comprising a base portion adapted to rest on a horizontal support surface and maintaining therein a holder panel in substantially horizontal position elevated above said support surface, said holder panel having a plurality of mutually spaced receptacle holes therein, a plurality of substantially tubular insert elastomeric material receptacles retentively engaged in the respective panel holes with their tubular axis oriented substantially vertically, said insert receptacles each including a tubular body portion extending through said holder panel and open at top and bottom, and a head portion adapted to seat against the top face of the holder panel, thereby to locate the insert receptacle vertically in relation to the panel, said insert receptacle body portion having an axially extending tubular socket bore of a size and a surrounding bore wall of an elastic yieldability adapting the body portion to elastically expand to accommodatively receive and thereupon retentively grip and frictionally retain a dental bur shank inserted downwardly therein, at least certain of the insert receptacles have an upper portion extending about the holder panel with a tubular socket bore adapted to hold dental burs having shanks of a first order of size, and having a lower portion extending below the holder panel with a tubular socket bore adapted to hold dental burs with shanks of a smaller order of size.

2. The holder defined in claim 1 wherein each of the insert receptacles have a tubular socket bore therein that is downwardly tapered, whereby to increase bur shank insertion resistance progressively as a function of insertion depth therein.

3. The holder defined in claim 1 wherein the tubular socket bores each have a downward taper, that of the upper portion starting at a level above that of the holder panel, and that of the lower portion continuing downwardly to a level below that of the holder panel.

4. The holder defined in claim 1 or 3 wherein the head portion of each receptacle comprises a flange surrounding the upper end of the body portion, and the open top of the receptacle bore is flared to form a widened entrance to facilitate insertion of burs into the receptacles.

5. The holder defined in claim 1 or 3 wherein the head portion of each receptacle comprises a flange surrounding the upper end of the body portion, and the open top of the receptacle bore is flared to form a widened entrance to facilitate insertion of burs into the receptacles, said holder base portion comprising a substantially vertical flange formation projecting downward from the holder panel to form a continuous enclosure protectively surrounding the space beneath the holder panel in which said receptacle holes are formed.

6. The holder defined in claim 1 or 3 wherein the holder base portion has at least one fitting therein adapted to engage a complemental fitting on an additional holder for maintaining the holders with their respective support panels in substantially coplanar relationship so as to permit handling the same as a composite unit.

* * * * *